United States Patent [19]

Lebowitz et al.

[11] 3,993,538
[45] Nov. 23, 1976

[54] PRODUCTION OF HIGH PURITY RADIOTHALLIUM

[75] Inventors: Elliot Lebowitz, Brookline, Mass.; Margaret W. Greene, Bellport, N.Y.

[73] Assignee: The United States of America as represented by the United States Energy Research and Development Administration, Washington, D.C.

[22] Filed: Jan. 27, 1976

[21] Appl. No.: 646,781

[52] U.S. Cl. .................................. 176/11; 176/16
[51] Int. Cl.² .......................................... G21G 1/10
[58] Field of Search ............................... 176/10–16

[56] References Cited
OTHER PUBLICATIONS
STI/Pub. 344, (vol. 1), 1973, p. 340.

Primary Examiner—Harvey E. Behrend
Attorney, Agent, or Firm—Dean E. Carlson; Leonard Belkin

[57] ABSTRACT

The method of producing high purity thallium-201 for use as a myocardial scanning agent comprising the steps of irradiating a thallium target with protons to give the reaction $^{203}Tl(p,3n)\ ^{201}Pb$, separating in ion exchange columns the lead from the thallium isotopes, permitting the lead to decay, and then purifying the thallium solution and converting the thallium present to thallous form in which it can be used.

4 Claims, No Drawings

PRODUCTION OF HIGH PURITY RADIOTHALLIUM

BACKGROUND OF THE INVENTION

This invention was made in the course of, or under a contract with the United States Energy Research and Development Administration, or its predecessor the United States Atomic Energy Commission.

Thallium-201 is a potentially useful radioisotope for various medical applications, including myocardial visualization and possible assessment of physiology, as a renal medullary scanning agent, and for tumor diagnosis.

Since $Tl^+$ is a good biological analog of potassium, it has the biological advantages of $K^+$ including high extraction by the myocardium on a single circulation. Furthermore, it has been observed that thallium activity remains in the myocardium even up to 18 hours postinjection. This removes a disadvantage of potassium from thallium, namely the rapid leakage of potassium from the myocardium. The ability to take many views may be crucial if it is necessary to view small infarcts in profile in order to visualize them. Delayed scans may yield improved resolution and the ability to look for leakage of thallium from the myocardium over several days of observation for myocardial infarction.

$^{201}Tl$, with a 73 hour half-life, decays by electron capture mainly to the ground state of stable mercury-201. It emits mercury K-X-rays of 69–83 keV in 93% abundance, and photons of 135 and 166 keV in 10% total abundance. The photons of $^{201}Tl$ are detected with high efficiency and resolution in a low-energy collimator, gamma camera detection system.

Furthermore, the 73 hour half-life gives $^{201}Tl$ a good shelf life, which is not only more convenient (by a considerable amount, in the cases of isotopes with half-lives of a few hours) than many of the other radioisotopes considered for myocardial visualization, but is also invaluable for availability for emergency use. The half-life of $^{201}Tl$ is consistent with a weekly shipment of this radiopharmaceutical from its supplier.

In view of the foregoing there has been interest in developing a practical and economical method of preparing high purity and specific activity thallium-201. Previous methods did not produce the thallium-201 in sufficient purity. A typical previous method was based on a formation of insoluble lead chloride, which as mentioned did not give the desired purity.

SUMMARY OF THE PRESENT INVENTION

The present invention involves a method for the production of high purity and specific activity thallium-201 in the form of a saline solution of thallous chloride.

A preferred embodiment of this invention incorporating the principles of this invention comprises the steps of irradiating a natural or enriched thallium-203 target to produce lead-201 by (proton, 3-neutron) interaction with thallium-203, dissolving and complexing the irradiated target and then subjecting it to successive cation and anion exchanges to separate thallium and lead with lead-201 and 203 as liquid elutant, allowing the lead in the liquid elutant to decay, and thereafter subjecting the liquid elutant to anion exchange to remove the thallium-201 and then converting the latter to its thallous form in which it is more soluble.

The process described above produces thallium-201 in thallous saline solution whose radioisotopic purity is at least 99% by weight.

It is thus a principal object of this invention to provide an improved method of producing high purity and specific activity thallium-201.

Other advantages and objects of this invention will hereafter become obvious from the following description of a preferred embodiment of this invention.

DESCRIPTION OF THE PREFERRED EMBODIMENT

A target of thallium-203 is irradiated by a beam of protons within the range of 20–30 MeV to produce lead-201 by the reaction $^{203}Tl(p,3n)$ $^{201}Pb$. The lead-201 has a half-life of 9.4 hours and is the parent of $^{201}Tl$. The target is in the form of a foil whose thickness is up to that which will attenuate the incoming beam to above 20 MeV at the back of the target.

The target employed may be fabricated from natural thallium which consists of about 30% thallium-203 and the remainder thallium-205, or the target may be enriched in the 203 isotope. Thallium-205 when irradiated in the target produces $^{203}Pb$ which has a half-life of 52 hours and decays to stable $^{203}Tl$.

The thallium target is irradiated for any desired period of time but inasmuch as the desired product has only a half life of 9.4 hours, it is seen that a point is reached where there is no gain in prolonging irradiation. A maximum practical period of irradiation would hence be equal to about two half lives, or 18 hours.

After irradiation, the target is dissolved in nitric acid to form soluble lead and thallium nitrates. After evaporation to dryness, an agent is then added to complex the lead present and hydrazine sulfate is added to reduce the thallium from any thallic form to the thallous which is more soluble. A suitable complexing agent is EDTA which is commercially available.

The solution is then passed through a cation exchange column to take out the thallium. The thallium remains on the column; because of its complexing the lead does not behave like a cation. The eluate thus consists largely of radioactive $^{203}Pb$ and $^{201}Pb$ in solution.

To remove any remaining traces of thallium from the solution, the latter is acidified by adding nitric acid and the thallium is oxidized to a thallic nitrate complex by adding NaClO, sodium hypochlorite. The solution is then passed through an anion exchange column where the thallium complex adheres to the column.

The eluate, which is a mixture of lead 201 and 203 in solution, is permitted to decay for a suitable period, typically 18 hours. The lead-201 decays with a 9.4 hour half-life to thallium-201, while the lead-203 decays with a 52 hour half-life to thallium-203.

In view of the large difference in half-lives, it is seen that after 18 hours the thallium-201 is for all practical purposes carrier-free. The thallium-203 present is barely detectable, and far below an amount considered toxic. The result is a solution which can be described as containing thallium-201 in substantial amounts and thallium-203 in insignificant amounts.

The solution is then passed through another anion exchange column where the $^{201}Tl$ is deposited out. Some $^{203}Tl$ is present but as already mentioned only in insignificant amounts. The column is washed by a hydrazine sulfate solution to remove the thallium, which also reduces the thallic ion to its thallous form.

To put the $^{201}$Tl into a useful form, the eluate is evaporated to dryness with nitric acid and then with hydrochloric acid to remove the nitric acid. The product is dissolved in sufficient sodium hydroxide to adjust the pH to 7, and then sterilized, the resulting solution being thallous chloride in saline solution.

It has been found that the presence of some thallic chloride, or the presence of some $^{203}$Tl does not interfere with the use of the final product as described above.

EXAMPLE $^{201}$Tl was produced by irradiating a natural thallium target in the external beam of the 60 inch Brookhaven cyclotron with 30 MeV protons. The nuclear reaction was $^{203}$Tl $(p,3n)$ $^{201}$Pb. The thallium target, fabricated from an ingot of 99.999% pure thallium metal, was 1.3 cm in diameter and weighed 0.7 grams. After irradiation, the thallium target was dissolved in concentrated nitric acid, then evaporated to dryness. This salt was then dissolved in 50 ml of 0.025 M EDTA at pH=4 and hydrazine sulfate and passed through a Bio-Rad Dowex 50 × 8 resin column (Na$^+$ form, 50–100 mesh, 2.5 × 6 cm). Most of the thallium target material adhered to the column and the eluate contained radioactive $^{203}$Pb and $^{201}$Pb. The eluate was acidified by adding an equal volume of conc. HNO$_3$ and the thallium was oxidized by the addition of "Clorox." Forty micrograms of Pb(NO$_3$)$_2$ carrier were added to the eluate and the solution passed thru a Bio-Rad Dowex 1 × 8 resin column (NO$_3$$^-$ form, 50–100 mesh, 2.5 × 6 cm). Thallium adhered to this column and the lead activities were eluted.

This eluate, containing $^{203}$Pb and $^{201}$Pb was allowed to stand overnight to permit the $^{201}$Pb to decay into $^{201}$Tl. It was then passed through another Bio-Rad Dowex 1 × 8 column, to which the $^{201}$Tl$^{+3}$ adhered and through which the lead activities were eluted. The $^{201}$Tl activity was then eluted with 20 ml of hot hydrazine-sulfate solution (20% W/V), reducing Tl$^{+3}$ to Tl$^{+1}$. This Tl$^{+1}$ eluate was evaporated to dryness twice with conc. HNO$_3$ and once with conc. HCl. The product was then dissolved in 5 ml of 10$^{-1}$M NaOH and the pH adjusted to 7 by further addition of NaOH. The product was sterilized by filtration into a sterile multi-injection bottle through a 0.22 micron sterilized millipore filter.

A Rhodamine B spot test was used to detect carrier thallium in the product before injection. The test can detect 0.02 $\mu$g of thallium. The sample tested is typically 1% of the total product; thus a negative spot test insures that less than 2 $\mu$g of thallium is present in the product. A few weeks after the $^{201}$Tl was produced, a complete chemical analysis of the product was performed by emission spectroscopy.

The radiochemical purity of the product was checked by solvent extraction. To demonstrate that the $^{201}$Tl was not in particulate form, the product was passed through a 250 A filter.

Radionuclidic purity was analyzed by multichannel pulse height analysis, utilizing a Ge(Li) detector. The gamma spectrum of the product was also followed for approximately one week to confirm the half-lives of the product and impurity gamma rays.

Product batches were tested for pyrogenicity by an independent laboratory. All glassware was rendered apyrogenic by autoclaving at 180° C for 3 hours.

Measurements of the excitation function (the production cross section as a function of energy) were performed by irradiating a stack of thin ($\approx$ 0.2 g/cm$^2$) foils of thallium and analyzing the activities produced by means of a Ge(Li) detector.

Emission spectroscopic chemical analysis of an entire product batch, is shown in Table I. The radioisotopic purity was $\geq$ 99%, as is shown in Table II. The product was at neutral pH, isotonic, sterile, and pyrogen free.

With a natural thallium target, the production rate of $^{201}$Tl was 0.7 mCi/$\mu$AH; or correspondingly higher with an enriched Tl-203 target.

TABLE I

| CHEMICAL ANALYSIS OF THE THALLIUM-201 PRODUCT | | | |
|---|---|---|---|
| Element | Quantity, $\mu$g | Element | Quantity, $\mu$g |
| Tl | <2 | Ni | <2 |
| Ca | 60 | Al | 1 |
| B | <2 | Mo | 0.2 |
| Mg | 1 | Cu | 6 |
| Mn | <0.2 | Ag | <0.2 |
| Si | 0.2 | Ti | 1 |
| Fe | 1 | V | 1 |

TABLE II

| RADIOISOTOPIC ANALYSIS OF THALLIUM-201 PRODUCT | | | | | |
|---|---|---|---|---|---|
| Isotope | t$^{1/2}$ | At time of preparation, % | 18 hrs later, % | 73 hrs later, % | 146 hrs later, % |
| Pb-203 | 52 hr | 1.6×10$^{-2}$ | 1.5×10$^{-2}$ | 1.2×10$^{-2}$ | 9 ×10$^{-3}$ |
| Tl-200 | 26 hr | 1.3×10$^{-1}$ | 9 ×10$^{-2}$ | 3.7×10$^{-2}$ | 1.1×10$^{-2}$ |
| Tl-202 | 12.2 d | 1.2×10$^{-1}$ | 1.4×10$^{-1}$ | 2.0×10$^{-1}$ | 3.4×10$^{-1}$ |

What is claimed is:

1. A method of producing at least 99% purity and high specific activity thallium-201 in its thallous form suitable for radiopharmaceutical applications comprising the steps of:
   a. irradiating a thallium target of at least 99.9% purity containing thallium-203 with a beam of protons in the range of 20-30 MeV and whose thickness is sufficiently great so that said beam is attenuated to a level not below 20 MeV for a sufficient length of time to produce lead-201 by the reaction $^{203}$Tl$(p,3n)$ $^{201}$Pb;
   b. dissolving the irradiated target;
   c. reducing any thallium present in the thallic form to its thallous state;
   d. subjecting the resulting solution to cation exchange to remove the thallium present and produce an eluate containing largely $^{203}$Pb and $^{201}$Pb in solution;
   e. acidifying the eluate;
   f. oxidizing any remaining traces of thallium to a thallic complex;
   g. subjecting the oxidized solution to anion exchange to remove the complexed thallium;
   h. permitting the mixture of lead 201 and 203 in the eluate to decay for no longer than about 24 hours to produce thallium-201 in substantial amounts and thallium-203 in insignificant amounts;

i. subjecting the decayed solution to another anion exchange wherein the thallium-201 is deposited out;

j. eluting the deposited $^{201}$Tl by converting any thallium in thallic form to its thallous form; and k. preparing and evaporating the thallium solution to produce dry thallium chloride.

2. The method of claim 1 in which the irradiated target is dissolved in nitric acid and the lead present is complexed by EDTA, and hydrazine sulfate is added to reduce the thallic ion to its thallous state.

3. The method of claim 3 in which the eluate from the cation exchange is acidified by adding nitric acid and the oxidizing is accomplished by adding NaClO.

4. The method of claim 3 in which the dried $^{201}$Tl is prepared for use by dissolving in sufficient sodium hydroxide to produce a pH of 7 to form a $^{201}$thallous chloride in saline solution.

* * * * *